United States Patent
Payne

(10) Patent No.: US 6,339,081 B1
(45) Date of Patent: *Jan. 15, 2002

(54) COMPOSITION AND USE

(75) Inventor: John David Payne, Manchester (GB)

(73) Assignee: Avecia Limited, Manchester (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/331,325

(22) PCT Filed: Dec. 5, 1997

(86) PCT No.: PCT/GB97/03379

§ 371 Date: Aug. 9, 1999

§ 102(e) Date: Aug. 9, 1999

(87) PCT Pub. No.: WO98/26665

PCT Pub. Date: Jun. 25, 1998

(30) Foreign Application Priority Data

Dec. 18, 1996 (GB) ............................................ 9626262

(51) Int. Cl.$^7$ ................................................. A01N 43/78
(52) U.S. Cl. ........................ 514/184; 548/101; 548/103; 548/105
(58) Field of Search ................................. 548/101, 103, 548/105; 514/184

(56) References Cited

U.S. PATENT DOCUMENTS 5,596,102 A * 1/1997 Austin ........................ 548/101

FOREIGN PATENT DOCUMENTS

| EP | 249 328 | 12/1987 |
| EP | 498 636 | 8/1992 |

* cited by examiner

Primary Examiner—Robert Gerstl
(74) Attorney, Agent, or Firm—Pillsbury Winthrop LLP

(57) ABSTRACT

A composition comprising (a) a metal complex of a cyclic thiohydroxamic acid such as the 2:1 zinc complex of 3-hydroxy-4-methylthiazol-2(3H)-thione and (b) a salt of the metal such as zinc chloride, acetate or oxide. The presence of component (b) gives enhanced microbiological activity.

21 Claims, No Drawings

COMPOSITION AND USE

This application is the national phase of international application PCT/GB97/03379 filed Dec. 5, 1997 which designated the U.S.

The present invention relates to stabilised compositions containing a metal complex of a cyclic thiohydroxamic acid or a 1-hydroxy-2-pyrrolidinthione and to improved antibacterial activity.

EP 249328 discloses metal complexes of cyclic thiohydroxamic acids and 1-hydroxy-2-pyrrolidinthiones and their use as industrial biocides. These metal complexes may also be used in personal care formulations as disclosed in EP 498636.

It has now been found that when these metal complexes are used in the presence of certain chemical compounds which act as ligands for the metal, the metal is removed at least in part from the metal complex and this results in a reduction in microbiological activity and/or a reduction in chemical stability, especially under acidic conditions. It has now been found that the metal complexes of cyclic thiohydroxamic acids (hereinafter 'CTHA') and the metal complexes of 1-hydroxy-2-pyrrolidinthiones (hereinafter 'HPT') may be stabilised by adding a salt of the metal and/or a metal complex of the metal derived from a ligand which is weaker than the CTHA or HPT. In many instances the metal complex of the CTHA and HPT exhibit increased antimicrobial activity in the presence of a salt of the metal, especially where the metal is zinc.

According to the invention there is provided a composition comprising (a) a metal complex of a compound of formula 1

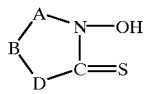

wherein
A is —$CR_2$— or —CR=;
B is —$CR_2$—, —CR= or >C=NR; or
A and B or B and D together form a 6-membered fused hydrocarbon ring;
D is sulphur, —NR—, —$CR_2$— or —CR=;
R is $C_{1-6}$-hydrocarbyl optionally substituted by halogen or two groups R together with the carbon atom to which they are attached form a 6-membered ring; and
(b) a salt of the metal and/or a metal complex of the metal obtainable from a ligand which is weaker than the compound of formula 1.

When R is hydrocarbyl, it may be phenyl. However, R is preferably alkyl, which may be linear or branched but is preferably linear. Examples of these alkyl groups are ethyl, isopropyl, n-butyl, tert-butyl, amyl, hexyl and especially methyl.

When A and B or B and D form a ring, the ring is preferably cyclohexenyl, cyclohexyl and especially phenyl.

When R is substituted by halogen, the substituent may be iodine, bromine or preferably chlorine.

When two groups R together with the carbon atom to which they are attached form a ring, the ring is preferably cyclohexyl.

The metal forming the complex with the compound of formula 1 may be any of the metals in groups 1b, 2a, 2b, 3a or 8 of the Periodic Table according to Mendeleef as published, for example, on the inside cover of the Handbook of Chemistry and Physics, The Chemical Rubber Company. It is preferred that the metal is from group 2b and that it is especially zinc.

The metal salt which is component (b) may be the salt of an inorganic or organic acid. In this context, a metal oxide is considered to be a salt of an inorganic acid. Preferred inorganic acids are hydrohalic acids, especially hydrochloric acid, nitric acid and sulphuric acid. It is particularly preferred that the salt is that of an organic acid or a metal oxide. Preferred organic acids are monocarboxylic acids, particularly those containing not greater than 10 and especially not greater than 6 carbon atoms excluding the —COOH group. Examples of organic acids are propionic and especially acetic acid.

When component (b) is a metal complex, it is preferably obtainable from an organic compound wherein the ligand(s) is a hydroxy group. The organic compound which forms a complex with the metal has a MW which is preferably not greater than 300, more preferably not greater than 250 and especially not greater than 200.

One preferred class of compounds of formula 1 is a cyclic thiohydroxamic acid wherein D is sulphur. Examples are
3-hydroxy-4-methylthiazol-2(3H)-thione,
3-hydroxy-4-phenylthiazol-2(3H)-thione,
3-hydroxy-4,5,6,7-tetrahydrobenzothiazol-2(3H)-thione,
5,5-dimethyl-1-hydroxy-4-imino-3-phenylimidazolidine-2-thione,
1-hydroxy-4-imino-3-phenyl-2-thiono-1,3-diazaspiro[4,5]decane,
1-hydroxy-5-methyl-4-phenylimidazoline-2-thione,
4,5-dimethyl-3-hydroxythiazol-2(3H)-thione,
4-ethyl-3-hydroxy-5-methylthiazol-2(3H)-thione,
4-(4-chlorophenyl)-3-hydroxythiazol-2(3H)-thione and
3-hydroxy-5-methyl-4-phenylthiazol-2(3H)-thione.

Another preferred class of compounds of formula 1 is a 1-hydroxy-2-pyrrolidinthione wherein D is —$CR_2$— or —CR=. Examples are
2-hydroxy-2,3-dihydro-1H-isoindol-1-thione,
1-hydroxy-2-pyrrolidinthione and
5,5-dimethyl-1-hydroxy-2-pyrrolidinthione.

Particularly useful effects have been obtained when component (a) is the 2:1 zinc complex of 3-hydroxy-4-methylthiazol-2(3H)-thione and component (b) is zinc acetate, zinc chloride or zinc oxide.

The composition according to the invention may be a mixture of component (a) and component (b) in solid form or it may further comprise a liquid medium when the composition comprises a dispersion of component (a) in the liquid medium containing component (b).

The liquid medium is preferably water.

The dispersion may also contain other adjuvants which are conventionally used to aid the dispersion of particulate solids in a liquid medium. These adjuvants include dispersants and compounds capable of forming a structured network of the liquid medium which aids the suspension of particulate solids (hereinafter "Structuring Agent").

The dispersant may be non-ionic, anionic, cationic or amphoteric. Preferred dispersants are non-ionic and are preferably ethoxylated fatty alcohols especially $C_{12-18}$-alkanols containing from 5 to 20 ethylene oxide units.

Preferred Structuring Agents are cellulose derivatives, naturally occurring clays and especially polysaccharide thickeners. Examples are hydroxyethylcellulose, Bentonite and Zanthan gum.

Component (b) may be soluble in or dispersible in the liquid medium but is preferably soluble.

The dispersion may be made by any means known to the art and may be made by grinding or milling component (a) in the presence of an attrition aid such as glass beads in order to reduce the particle size. The particle size of component (a) is preferably reduced below 20 $\mu$, more preferably below 10 $\mu$ and especially to below 3 $\mu$. The fine particle of component (a) may then be added to component (b) and the liquid medium. Alternatively, components (a) and (b) may be ground or milled together and then added to the liquid medium. It is preferred, however, to grind or mill component (a) in the liquid medium containing component (b).

The amount of component (b) relative to component (a) may be just sufficient to provide enhanced microbiological activity and/or a stabilising effect but is preferably present in larger amounts. Preferably the weight ratio of component (b) to component (a) is between 5:1 and 1:5, more preferably between 3:1 and 1:2 and especially between 2:1 and 1:1.

The amount of component (a) in the dispersion is from 1 to 30% relative to the total weight of the dispersion. Preferably the amount of component (a) is not less than 3% and especially not less than 5% relative to the total weight of the dispersion. It is also preferred that the amount of component (a) is not greater than 20%, more preferably not greater than 15% and especially not greater than 10% relative to the total weight of the dispersion.

The amount of dispersant depends on the amount of component (a) but is generally between 5% and 200% based on the weight of component (a). Preferably the amount of dispersant is not greater than 100% and especially not greater than 50% based on the weight of component (a).

The amount of Structuring Agent, when present, depends on the total weight of the dispersion and is preferably not less than 0.05%, more preferably not less than 0.1% and especially not less than 0.2% based on the total weight of the dispersion. It is also preferred that the amount of Structuring Agent is not greater than 1% and especially not greater than 0.5% based on the total weight of dispersion.

The pH value of the dispersion can be from pH3 to pH10 but is preferably not less than 5, more preferably not less than 6 and especially not less than 6.5. It is also preferred that the pH is not greater than 9 and especially not greater than 8.

When the pH value of the dispersion needs to be adjusted this may be carried out by adding any appropriate organic or inorganic acid or base. However, when component (b) is an inorganic or organic metal salt it is advantageous to use the same acid as that providing the metal salt when reducing the pH of the dispersion.

When the dispersion contains a Structuring Agent, the viscosity of the dispersion is preferably not less than 1000, more preferably not less than 1200 and especially not less than 1500 centipoise as measured by Brookfield viscometer using Spindle No. 2 and a rotational speed of 10 rpm at 20° C. The viscosity is also preferably not greater than 4,000, more preferably not greater than 3,500 and especially not greater than 3,000 centipoise at 20° C.

The composition may contain additional biologically active compounds especially where it is desirable to increase the spectrum of activity. In some instances an enhanced activity is obtained.

Examples of other antimicrobial compounds which may be used, together with the composition are quaternary ammonium compounds such as N,N-diethyl-N-dodecyl-N-benzylammonium chloride; N,N-dimethyl-N-octadecyl-N-(dimethylbenzyl)ammonium chloride; N,N-dimethyl-N,N-didecylammonium chloride; N,N-dimethyl-N,N-didodecylammonium chloride; N,N,N-trimethyl-N-tetradecylammonium chloride; N-benzyl-N,N-dimethyl-N-($C_{12}$–$C_{18}$ alkyl)ammonium chloride; N-(dichlorobenzyl)-N,-N-dimethyl-N-dodecylammonium chloride; N-hexadecylpyridinium chloride; N-hexadecylpyridinium bromide; N-hexadecyl-N,N,N-trimethylammonium bromide; N-dodecylpyridinium chloride; N-dodecylpyridinium bisulphate; N-benzyl-N-dodecyl-N,N-bis(beta-hydroxyethyl)ammonium chloride; N-dodecyl-N-benzyl-N,N-dimethylammonium chloride; N-benzyl-N,N-dimethyl-N-($C_{12}$–$C_{18}$ alkyl) ammonium chloride; N-dodecyl-N,N-dimethyl-N-ethylammonium ethylsulphate; N-dodecyl-N,N-dimethyl-N-(1-naphthylmethyl)ammonium chloride; N-hexadecyl-N,N-dimethyl-N-benzylammonium chloride; N-dodecyl-N,N-dimethyl-N-benzylammonium chloride and 1-(3-chloroallyl)-3,5,7-triaza-1-azonia-adamantane chloride; urea derivatives such as 1,3-bis(hydroxymethyl)-5,5-dimethylhydantoin; bis(hydroxymethyl)urea; 3-(3,4-dichlorophenyl)-1,1-dimethylurea; 3-(4-isopropylphenyl)-1,1-dimethylurea; tetrakis (hydroxymethyl)-acetylene diurea; 1-(hydroxymethyl)-5,5-dimethylhydantoin and imidazolidinylurea; amino compounds such as 1,3-bis(2-ethyl-hexyl)-5-methyl-5-aminohexahydro-pyrimidine; hexamethylenetetramine; 1,3-bis(4-aminophenoxy)propane; and 2-[(hydroxymethyl)-amino]ethanol; imidazole derivatives such as 1[2-(2,4-dichloro-phenyl)-2-(2-propenyloxy)ethyl]-1H-imidazole; 2-(methoxycarbonyl-amino)-benzimidazole; nitrile compounds such as 2-bromo-2-bromomethyl-glutaronitrile, 1,2-dibromo-2,4-dicyanatobutane, 2-chloro-2-chloro-methylglutaronitrile; 2,4,5,6-tetra-chloroisophthalodinitrile; thiocyanate derivatives such as methylene(bis)thiocyanate; tin compounds or complexes such as tributyltinoxide, chloride, naphthoate, benzoate or 2-hydroxybenzoate; isothiazolin-3-ones such as 4,5-trimethylene-4-isothiazolin-3-one, 2-methyl-4,5-trimethylene-4-isothiazolin-3-one, 2-methylisothiazolin-3-one, 5-chloro-2-methyl-isothiazolin-3-one, benzisothiazolin-3-one, 2-n-butylbenzisothiazolin-3-one, 2-n-hexylbenzisothiazolin-3-one, 2-(2-ethylbutyl) benzisothiazolin-3-one, 2-(2-phenylethyl) benzisothiazolin-3-one, 2-(2-ethylhexyl)benzisothiazolin-3-one; 2-methylbenzisothiazolin-3-one, 2-octylisothiazolin-3-one, 4,5-dichloro-2-octylisothiazolin-3-one; thiazole derivatives such as 2-(thiocyanomethylthio)-benzthiazole and mercaptobenzthiazole; nitro compounds such as tris (hydroxymethyl)nitromethane; 5-bromo-5-nitro-1,3-dioxane and 2-bromo-2-nitropropane-1,3-diol; iodine compounds such as iodo propynyl butyl carbamate and tri-iodo allyl alcohol; aldehydes and derivatives such as glutaraldehyde (pentanedial), p-chlorophenyl-3-iodopropargyl, formaldehyde and glyoxal; amides such as chloracetamide; N,N-bis(hydroxymethyl)chloracetamide; N-hydroxymethylchloracetamide and dithio-2,2-bis (benzmethylamide); guanidine derivatives such as poly (hexamethylenebiguanide) and 1,6-hexamethylene-bis[5-(4-chlorophenyl)biguanide]; thiones such as 3,5-dimethyltetrahydro-1,3,5-2H-thiodiazine-2-thione; triazine derivatives such as hexahydrotriazine and 1,3,5-tri-(hydroxyethyl)-1,3,5-hexahydrotriazine, 6-chloro-2,4-diethyl-amino-s-triazine and 4-cyclopropylamino-2-methylthio-6-t-butylamino-s-triazine; oxazolidine and derivatives thereof such as bis-oxazolidine; furan and derivatives thereof such as 2,5-dihydro-2,5-dialkoxy-2,5-dialkylfuran; carboxylic acids and the salts and esters thereof such as sorbic acid and 4-hydroxybenzoic acid and their salts and esters; phenol and derivatives thereof such as 5-chloro-2-(2,4-dichlorophenoxy)phenol; thio-bis(4-chlorophenol) and 2-phenylphenol, 2,4,4'-trichloro-2'-hydroxydiphenylether; sulphone derivatives such as diiodomethyl-paratolyl sulphone; 2,3,5,6-tetrachloro-4-(methylsulphonyl) pyridine and hexachlorodimethyl sulphone; thioamides such as dimethyidithiocarbamate and its metal complexes, ethylenebisdithiocarbamate and its metal complexes, and 2-mercapto-pyridine-N-oxide and its metal complexes.

The composition and dispersion of the present invention is microbiologically active and can be used to protect any medium against microbiological degradation. The medium may be an industrial medium such as a latex, paint, cooling tower water, paper mill liquor, sealant, pipe joint tapes, adhesive, drilling mud or cutting fluid. The medium may also be any personal care formulation, especially those disclosed in EP 498,636 and especially shampoo formulations. The medium may also be a solid surface such as wood, leather and particularly any surface associated with the preparation of foodstuffs.

The invention is further illustrated by the following examples wherein all references to amounts are in parts by weight unless expressed to the contrary.

EXAMPLE 1

Aliquots (25 parts) of unpreserved latex containing 50% by weight solids of a copolymer of 2-ethylhexylacrylate/acrylic acid at pH 8.5 were formulated with zinc acetate and the 2:1 zinc complex of 3-hydroxy4-methyl thiazol-2(3H)-thione in the amounts shown in Table 1 below. After formulation, each aliquot was stored at 20° C. for 1 week prior to inoculation with a mixed bacterial culture.

The bacterial culture was prepared by culturing the following seven bacteria in nutrient agar for 24 hours at 30° C.

*Proteus rettgeri*

*Serratia marcescens*

*Aeromonas hydrorhila*

*Alcalipenes species*

*Pseudomonas aeruginosa*

*Pseudomonas putida*

*Pseudomonas cepacia*

Each of the individual bacterium was prepared at a concentration of $10^8$ cells/ml in quarter strength Ringers solution by means of a Thoma counting chamber. The mixed inoculum was prepared by mixing equal volumes of the cultures containing the individual bacterium.

The latex aliquots were repeatedly inoculated at 0, 7 and 14 day intervals with 0.5 ml mixed inoculum ($2 \times 10^6$ cells/ml) and incubated at 30° C. The number of viable bacteria was determined by streaking a small portion of each aliquot of latex onto nutrient agar after 3, 5 and 7 days followed by visible assessment after incubation for 2 days at 30° C. The results are given in Table 1 and shown that both zinc acetate and zinc chloride exhibit no antimicrobial activity and that the activity of the 2:1 zinc complex of 3-hydroxy-4-methylthiazol-2(3H)-thione is significantly enhanced in the presence of both zinc salts especially after repeated challenge. It is believed that the reduced activity of the thione metal complex in the absence of zinc salts is due to the presence of a phosphate water softener in the latex.

TABLE 1

| Amount (ppm) | | | First inoculum (days) | | | Second inoculum (days) | | | Third inoculum (days) | | |
|---|---|---|---|---|---|---|---|---|---|---|---|
| ZHMT | ZA | ZC | 3 | 5 | 7 | 3 | 5 | 7 | 3 | 5 | 7 |
| 25 | 0 | 0 | − | − | − | C | C | C | C | C | C |
| 50 | 0 | 0 | ++ | − | − | ++ | + | + | C | C | C |
| 100 | 0 | 0 | ++ | − | − | ++ | + | − | ++ | ++ | ++ |
| 200 | 0 | 0 | + | − | − | ++ | + | − | ++ | ++ | ++ |

TABLE 1-continued

| Amount (ppm) | | | First inoculum (days) | | | Second inoculum (days) | | | Third inoculum (days) | | |
|---|---|---|---|---|---|---|---|---|---|---|---|
| ZHMT | ZA | ZC | 3 | 5 | 7 | 3 | 5 | 7 | 3 | 5 | 7 |
| 25 | 25 | 0 | − | − | − | C | C | C | C | C | C |
| 50 | 50 | 0 | ++ | − | − | ++ | − | − | ++ | − | − |
| 100 | 100 | 0 | ++ | − | − | ++ | − | − | ++ | + | − |
| 200 | 200 | 0 | + | − | − | + | − | − | ++ | − | − |
| 25 | 0 | 25 | + | − | − | C | C | C | C | C | C |
| 50 | 0 | 50 | + | + | − | ++ | − | − | ++ | − | − |
| 100 | 0 | 100 | + | − | − | ++ | + | − | ++ | + | − |
| 200 | 0 | 200 | + | − | − | − | − | − | + | − | − |
| 0 | 200 | 0 | − | − | − | ++ | ++ | ++ | ++ | ++ | ++ |
| 0 | 0 | 200 | + | − | − | ++ | ++ | ++ | C | C | C |
| 0 | 0 | 0 | + | − | − | ++ | ++ | ++ | C | C | C |

Footnote to Table 1
ZHMT is the 2:1 zinc complex of 3-hydroxy-4-methylthiazol-2(3H)-thione
ZA is zinc acetate
ZC is zinc chloride
C is confluent growth over the surface
− is no visible colonies
+ is few visible colonies
++ is clusters of discreet colonies

EXAMPLE 2

A $C_{14}$-alcoholethoxylate dispersant (0.5 parts, Synperonic A11 ex. ICI), water (50 parts), zinc acetate (5 parts) and the 2:1 zinc complex of 3-hydroxy-4-methylthiazol-2(3H)-thione (5 parts) were thoroughly mixed using a Silverson mixer. The dispersion was then milled in a horizontal bead mill in the presence of 1 mm diameter Ballotini glass beads until the mean particle size of the metal complex was below $5\mu$. The dispersion was then separated from the glass beads and then the remainder of the water and Xantham gum (0.3 parts) were added with high shear mixing using a Silverson mixer. A stable white dispersion was obtained containing 5% metal complex, 5% zinc acetate, 0.5% dispersant and 0.3% Xantham gum which exhibited excellent stability when stored at 40° C. for 1 month.

A similar stable dispersion was obtained when the zinc acetate was replaced by the same amount of zinc chloride.

EXAMPLE 3

25 ml Aliquots of a contaminated matt paint millbase were formulated with the 2:1 zinc complex of 3-hydroxy-4-methylthiazol-2(3H)-thione and zinc acetate as shown in Table 2 below. The number of variable cells was determined by streaking a small portion of each aliquot of millbase onto nutrient agar after 5, 7 and 14 days. The number of cells was determined by visible assessment following incubation for 2 days at 30° C. The results show that zinc acetate increases the bacterial activity of the metal complex.

TABLE 2

| Amount (ppm) | | Viable cells after (days) | | |
|---|---|---|---|---|
| ZHPT | ZA | 5 | 7 | 14 |
| 25 | 0 | C | C | C |
| 50 | 0 | C | C | — |
| 25 | 25 | C | — | — |
| 50 | 50 | C | — | — |

Footnote to Table 2
ZHPT, ZA, C and — are as explained in the footnote to Table 1.

EXAMPLE 4

Fractional Inhibitory Concentration (FIC) of ZHMT

The gram negative bacterium, *Pseudomonas aeruginosa* NCIB 10421 was grown in nutrient broth to stationary phase during 18 hours and contained approximately $10^9$ organisms/ml. A 0.1% (v/v) inoculum was used to seed fresh nutrient broth and 100 µl was then added to each well of a microtitre plate, except for the first well which contained 200 µl.

Solutions of zinc acetate (ZnAc) and the 2:1 zinc complex of 3-hydroxy-4-methylthiazol-2(3H)-thione (ZHMT), respectively, were prepared in nutrient broth at twice the final concentration to be used in the microtitre array. A microtitre array was prepared with concentration of zinc acetate and ZHMT from twice the MIC down to zero concentration in a 10×10 array. Since the array contains only 96 wells, the highest and lowest concentration of the zinc acetate and ZHMT were omitted. The dilution of the ZHMT was doubled across the ordinate axis of the array by transferring 100 µl aliquots so that the final volume in each well was 200 µl. The microtitre plate was then incubated for 16 to 24 hours at 37° C. and the presence of bacterial growth assessed visually.

The Minimum Inhibitory Concentrations (MIC) for zinc acetate and ZMHT were 250 ppm and 32 ppm, respectively.

The FIC is defined as the sum of the fractional inhibitory concentration of each component. The FIC of the individual component is the ratio of the concentration of the component in the binary mixture divided by its MIC.

The FIC values obtained are given in Table 3 below.

TABLE 3

| Relative conc. of ZHMT | Relative conc. of ZnAc | FIC |
|---|---|---|
| 1 | 0 | 1 |
| 0.28 | 0.17 | 0.45 |
| 0.14 | 0.5 | 0.64 |
| 0 | 1 | 1 |

These results indicate that the composition of ZHMT and ZnAc exhibits marked synergy and that the optimal concentrations of ZHMT and ZnAc are 9 ppm and 43 ppm respectively compared with their MIC values of 32 ppm and 250 ppm, respectively.

When the ZnAc was replaced by the same weight of cupric chloride, magnesium chloride and manganese chloride, the ZHMT exhibited no synergy. When the ZnAc was replaced with half the weight of ferric chloride the latter exhibited an antagonistic effect on the ZHMT.

When the ZHMT was replaced by the 2:1 zinc complex of 1-hydroxypyridine-2-thione, no synergy was observed with ZnAc.

EXAMPLE 5

A starch adhesive was prepared containing polyvinyl acetate (42%), corn starch (10%), calcium sulphate (10%), calcium carbonate (15%), softener (3%), polyvinyl alcohol (10%) and cellulose (10%). This starch adhesive was treated with a 5% aqueous dispersion of the 2:1 zinc complex of 3-hydroxy-4-methylthiazol-2(3H)-thione (ZHMT) optionally containing an equal weight of zinc acetate relative to the weight of ZHMT.

An inoculum was prepared containing the following micro-organisms:

*Proteus rettgeri,*
*Serretia marcescans,*
*Aeromonas hydrophila,*
Alcaligenes species
*Pseudomonas aeruginosa,*
*Pseudomonas putida,* and
*Pseudomonas cepacia*

Each of the individual bacterium was cultured in nutrient agar and incubated at 30° C. for 24 hours followed by suspension in quarter strength Ringers solution by means of a Thoma countering chamber to give $10^8$ cells/ml. A mixed inoculum was prepared by combining equal volumes.

An aliquot of the starch containing the ZHMT, and optionally zinc acetate, was inoculated weekly with 0.5 ml of the mixed inoculum on three occasions to give $2 \times 10^6$ cells/ml. The aliquots were then incubated at 30° C. and examined for bacterial growth by streaking a small sample onto nutrient agar and incubating at 30° C. for 2 days prior to visual examination. The results are given in Table 4 below:

TABLE 4

| Preservative | Conc. | First inoculum Days | | Second inoculum Days | | Third inoculum Days | |
|---|---|---|---|---|---|---|---|
| | | 4 | 7 | 4 | 7 | 5 | 7 |
| 5% aqueous ZHMT | 10 | ++ | − | +++ | − | +++ | +++ |
| | 25 | +++ | − | +++ | ++ | +++ | +++ |
| | 50 | +++ | − | +++ | ++ | +++ | +++ |
| | 100 | +++ | − | +++ | − | +++ | +++ |
| 5% aqueous ZHMT with zinc acetate | 10 | − | − | + | + | +++ | +++ |
| | 25 | + | − | + | − | +++ | − |
| | 50 | + | − | ++ | + | +++ | − |
| | 100 | − | − | − | − | − | − |
| Control | — | +++ | + | +++ | + | +++ | +++ |

Footnote to Table 4
− = no growth (no visible colonies)
+ = light growth (a few visible colonies)
++ = moderate growth (discrete colonies visible, some coalescence)
+++ = dense, confluent growth (coalescing colonies visible throughout streak)

The results show that the aqueous dispersion of ZHMT controlled bacterial growth following two inoculations but not after the third inoculation even at the 100 ppm level. In the presence of zinc acetate, the ZHMT inhibited bacterial growth at the 25 ppm level even after the third inoculation.

EXAMPLE 6

ZHMT with Oxide in Paint

Aliquots of a styrene-acrylic emulsion paint were treated with the 2:1 zinc complex of 3-hydroxy-4-methylthiazol-2 (3H)-thione (ZHMT) optionally containing zinc acetate (ZnAc) or zinc oxide (ZnO). These aliquots were challenged with the mixed inoculum described in Example 5 and examined for bacterial growth as described in this previous example. The results are given in Table 5 below:

TABLE 5

| Preserv-ative | Conc. | First Inoculum Days | | Second Inoculum Days | | | Third Inoculum Days | | |
|---|---|---|---|---|---|---|---|---|---|
| | | 4 | 7 | 4 | 7 | 14 | 4 | 7 | 21 |
| ZHMT | 10 | − | − | +++ | +++ | +++ | +++ | +++ | +++ |
| | 25 | − | − | +++ | +++ | +++ | +++ | +++ | +++ |
| | 50 | − | − | +++ | +++ | +++ | +++ | +++ | +++ |
| | 100 | − | − | +++ | +++ | +++ | +++ | +++ | +++ |
| | 200 | − | − | ++ | ++ | ++ | +++ | +++ | +++ |
| ZHMT with | 10 | − | − | +++ | +++ | +++ | +++ | +++ | +++ |
| | 25 | − | − | +++ | +++ | +++ | +++ | +++ | +++ |

TABLE 5-continued

| Preservative | Conc. | First Inoculum Days | | Second Inoculum Days | | | Third Inoculum Days | | |
|---|---|---|---|---|---|---|---|---|---|
| | | 4 | 7 | 4 | 7 | 14 | 4 | 7 | 21 |
| ZnAc (1:1) | 50 | – | – | ++ | +++ | +++ | +++ | +++ | +++ |
| | 100 | – | – | – | – | – | – | – | – |
| | 200 | – | – | – | – | – | – | – | – |
| ZHMT with ZnAc (1:4) | 25 | – | – | +++ | +++ | +++ | +++ | +++ | +++ |
| | 50 | – | – | +++ | +++ | +++ | +++ | +++ | +++ |
| | 100 | – | – | – | – | – | – | – | – |
| | 200 | – | – | – | – | – | – | – | – |
| ZHMT with ZnO (1:1) | 25 | – | – | +++ | +++ | +++ | +++ | +++ | +++ |
| | 50 | – | – | +++ | +++ | +++ | +++ | +++ | +++ |
| | 100 | – | – | – | – | – | – | – | – |
| | 200 | – | – | – | – | – | – | – | – |
| ZHMT with ZnO (1:4) | 25 | – | – | +++ | +++ | +++ | +++ | +++ | +++ |
| | 50 | – | – | – | – | – | – | – | – |
| | 100 | – | – | – | – | – | – | – | – |
| | 200 | – | – | – | – | – | – | – | – |
| Control | — | +++ | +++ | +++ | +++ | +++ | +++ | +++ | +++ |

Footnote to Table 5
-, +, ++ and +++ are as described in the footnote to Table 4.

These results indicate that ZHMT does not preserve the paint at the 200 ppm level whereas in the presence of an equal amount of zinc acetate the paint is preserved at the 100 ppm level. In the presence of an equal weight of zinc oxide, the paint is preserved with 100 ppm ZHMT but this reduces to 50 ppm in the presence of a four-fold excess of zinc oxide.

What is claimed is:

1. A composition comprising
   (a) a metal complex of a compound of formula 1

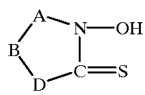

wherein
   A is —CR$_2$— or —CR=;
   B is —CR$_2$—, —CR= or >C=NR; or
   A and B or B and D together form a 6-membered fused hydrocarbon ring;
   D is sulphur, —NR—, —CR$_2$— or =CR=;
   R is H or C$_{1-6}$-hydrocarbyl optionally substituted by halogen or two groups R together with the carbon atom to which they are attached form a 6-membered ring;
   (b) a salt of the metal;
   (c) a dispersant and
   (d) a liquid carrier, the weight ratio of (a) to (b) being from 5:1 to 1:5 and such as to provide stability and enhanced microbiological activity of (a).

2. A composition as claimed in claim 1 wherein the metal is from groups 1a, 2a, 2b, 3a or 8 of the Periodic Table.

3. A composition as claimed in either claim 1 or claim 2 wherein the metal is zinc.

4. A composition as claimed in claim 1 wherein the compound of formula 1 is selected from the group consisting of:
   3-hydroxy-4-methylthiazol-2(3H)-thione,
   3-hydroxy-4-phenylthiazol-2(3H)-thione,
   3-hydroxy-4,5,6,7-tetrahydrobenzothiazol-2(3H)-thione,
   5,5-dimethyl-1-hydroxy-4-imino-3-phenylimidazolidine-2-thione,
   1-hydroxy-4-imino-3-phenyl-2-thiono-1,3-diazaspiro[4,5]decane,
   1-hydroxy-5-methyl-4-phenylimidazoline-2-thione,
   4,5-dimethyl-3-hydroxythiazol-2(3H)-thione,
   4-ethyl-3-hydroxy-5-methylthiazol-2(3H)-thione,
   4-(4-chlorophenyl)-3-hydroxythiazol-2(3H)-thione,
   3-hydroxy-5-methyl-4-phenylthiazol-2(3H)-thione,
   2-hydroxy-2,3-dihydro-1H-isoindol-1-thione,
   1-hydroxy-2-pyrrolidinthione and
   5,5-dimethyl-1-hydroxy-2-pyrrolidinthione.

5. A composition as claimed in any one of claims 1 to 4 wherein component (b) is a chloride, acetate or metal oxide.

6. A composition as claimed in claim 1 wherein component (a) is the 2:1 zinc complex of 3-hydroxy-4-methyl-thiazol-2-(3H)-thione and component (b) is zinc chloride, zinc acetate or zinc oxide.

7. A composition as claimed in claim 1 wherein the dispersant is a C$_{12-18}$-alkanol containing from 5 to 20 ethyleneoxide units.

8. A composition as claimed in claim 1 which further comprises a Structuring Agent.

9. A composition as claimed in claim 8 wherein the Structuring Agent is Xanthan Gum.

10. A method for inhibiting the growth of microorganisms in, or on, a medium which is susceptible to microbiological deterioration which comprises treating the medium with
    (a) a metal complex of a compound of formula 1

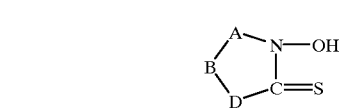

wherein
    A is —CR$_2$— or —CR=;
    B is —CR$_2$—, —CR= or >C=NR; or
    A and B or B and D together form a 6-membered fused hydrocarbon ring;
    D is sulphur, —NR—, —CR$_2$— or —CR=;
    R is C$_{1-6}$-hydrocarbyl optionally substituted by halogen or two groups R together with the carbon atom to which they are attached form a 6-membered ring; and
    (b) a salt of the metal.

11. A medium containing a composition as claimed in claims 1 or 6.

12. A medium as claimed in claim 11 which is a paint, latex or adhesive.

13. A composition comprising
    (a) a metal complex of a compound of formula 1

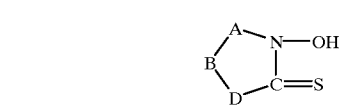

wherein
    A is —CR$_2$— or —CR=;
    B is —CR$_2$—, —CR= or >C=NR; or
    A and B or B and D together form a 6-membered fused hydrocarbon ring;
    D is sulphur, —NR—, —CR$_2$— or =CR=;

R is H or $C_{1-6}$-hydrocarbyl optionally substituted by halogen or two groups R together with the carbon atom to which they are attached form a 6-membered ring;

(b) a salt of the metal;

provided component (b) is not a sulphate salt of the metal, the weight ratio of (a) to (b) being from 5:1 to 1:5 and such as to provide stability and enhanced microbiological activity of (a); and (c) a dispersant.

14. A composition comprising (a) a metal complex of a compound of formula 1

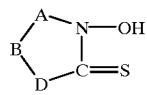

wherein

A is $-CR_2-$ or $-CR=$;

B is $-CR_2-$, $-CR=$ or $>C=NR$; or

A and B or B and D together form a 6-membered fused hydrocarbon ring;

D is sulphur, $-NR-$, $-CR_2-$ or $=CR=$;

R is H or $C_{1-6}$-hydrocarbyl optionally substituted by halogen or two groups R together with the carbon atom to which they are attached form a 6-membered ring;

(b) a compound selected from the group consisting of (i), (ii) and (iii):

(i) a salt of the metal selected from a salt of a hydrohalic acid, a salt of nitric acid and a salt of an organic acid;

(ii) an oxide of the metal;

(iii) a complex of the metal obtainable from an organic compound wherein the ligand(s) is a hydroxy group, the weight ratio of (a) to (b) being from 5:1 to 1:5 and such as to provide stability and enhanced microbiological activity of (a); and (c) a dispersant.

15. A composition as claimed in either claim 13 or claim 14 wherein the metal is from groups 1a, 2a, 2b, 3a or 8 of the Periodic Table.

16. A composition as claimed in either claim 13 or claim 14 wherein the metal is zinc.

17. A composition as claimed in either claim 13 or claim 14 wherein the compound of formula 1 is selected from the group consisting of:

3-hydroxy-4-methylthiazol-2(3H)-thione, 3-hydroxy-4-phenylthiazol-2(3H)-thione, 3-hydroxy-4,5,6,7-tetrahydrobenzothiazol-2(3H)-thione, 5,5-dimethyl-1-hydroxy-4-imino-3-phenylimidazolidine-2-thione, 1-hydroxy-4-imino-3-phenyl-2-thiono-1,3-diazaspiro[4,5]decane, 1-hydroxy-5-methyl-4-phenylimidazoline-2-thione, 4,5-dimethyl-3-hydroxythiazol-2(3H)-thione, 4-ethyl-3-hydroxy-5-methylthiazol-2(3H)-thione, 4-(4-chlorophenyl)-3-hydroxythiazol-2(3H)-thione, 3-hydroxy-5-methyl-4-phenylthiazol-2(3H)-thione, 2-hydroxy-2,3-dihydro-1H-isoindol-1-thione, 1-hydroxy-2-pyrrolidinthione and 5,5-dimethyl-1-hydroxy-2-pyrrolidinthione.

18. A composition as claimed in either claim 13 or claim 14 wherein component (b) is a chloride, acetate or metal oxide.

19. A composition according to either claim 13 or claim 14 wherein component (a) is the 2:1 zinc complex of 3-hydroxy-4-methyl-thiazol-2-(3H)-thione and component (b) is zinc chloride, zinc acetate or zinc oxide.

20. A medium containing a composition according to either claim 13 or claim 14.

21. A composition according to any one of claims 1, 13 or 14 further comprising a liquid medium.

* * * * *